(12) United States Patent
Johansen et al.

(10) Patent No.: US 11,484,040 B2
(45) Date of Patent: Nov. 1, 2022

(54) AMPICILLIN RESISTANT TEXTURIZING LACTIC ACID BACTERIA STRAINS

(71) Applicant: Chr. Hansen A/S, Hoersholm (DK)

(72) Inventors: Eric Johansen, Hoersholm (DK); Kim Ib Soerensen, Farum (DK); Annette Kibenich, Hvidovre (DK)

(73) Assignee: Chr. Hansen A/S, Hoersholm (DK)

( * ) Notice: Subject to any disclaimer, the term of this patent is extended or adjusted under 35 U.S.C. 154(b) by 248 days.

(21) Appl. No.: 16/429,468

(22) Filed: Jun. 3, 2019

(65) Prior Publication Data

US 2019/0281847 A1    Sep. 19, 2019

Related U.S. Application Data

(62) Division of application No. 14/395,615, filed as application No. PCT/EP2013/058335 on Apr. 23, 2013, now Pat. No. 10,716,313.

(30) Foreign Application Priority Data

Apr. 23, 2012    (EP) .................................... 12165134

(51) Int. Cl.
| | | |
|---|---|---|
| C12N 1/20 | (2006.01) | |
| A23C 9/123 | (2006.01) | |
| C12N 15/01 | (2006.01) | |
| C12N 1/12 | (2006.01) | |
| C12R 1/225 | (2006.01) | |

(52) U.S. Cl.
CPC .............. *A23C 9/1238* (2013.01); *C12N 1/12* (2013.01); *C12N 1/20* (2013.01); *C12N 15/01* (2013.01); *A23C 2220/202* (2013.01); *A23Y 2220/15* (2013.01); *A23Y 2220/29* (2013.01); *A23Y 2240/75* (2013.01); *C12N 1/205* (2021.05); *C12R 2001/225* (2021.05)

(58) Field of Classification Search
None
See application file for complete search history.

(56) References Cited

U.S. PATENT DOCUMENTS

| | | | | |
|---|---|---|---|---|
| 9,428,734 | B2 * | 8/2016 | De Crecy ................ | C12N 5/04 |
| 2005/0158423 | A1 * | 7/2005 | Geis ...................... | A23C 9/1236 |
| | | | | 426/43 |
| 2006/0099197 | A1 | 5/2006 | Farmer | |
| 2015/0079232 | A1 | 3/2015 | Johansen et al. | |

FOREIGN PATENT DOCUMENTS

| | | |
|---|---|---|
| JP | 2001-520035 A | 10/2001 |
| JP | 2004-357528 A | 12/2004 |
| JP | 2006-288290 A | 10/2006 |
| JP | 2008-245576 A | 10/2008 |
| WO | WO 99/20739 A2 | 4/1999 |
| WO | WO 2011/092300 A1 | 8/2011 |
| WO | WO-2012/052557 A1 | 4/2012 |
| WO | WO-2013/160270 A1 | 10/2013 |

OTHER PUBLICATIONS

Guzzo, Biotechnical applications of small heat shock proteins from bacteria, The International Journal of Biochemistry & Cell Biology 44 (2012) 1698-1705 (Year: 2012).*
Studies on Yogurt Production Using Lactobacillus bulgaricus and *Streptococcus thermophilus* Isolated From Market Yogurt, J. Sylhet Agril. Univ. 3(2):307-313, 2016.*
Gaze et al., Novel Insights into Selection for Antibiotic Resistance in Complex Microbial Communities, American Society for Microbiology, vol. 9, issue 4, 2018.*
Wei, et al., Antibiotic Resistance of Lactic Acid Bacteria Isolated From Chinese Yogurt, J. Dairy Sc, 95:4775-4783 2012.*
Hummel et al, "Antibiotic Resistances of Starter and Probiotic Strains of Lactic Acid Bacteria", Applied and Environmental Microbiology, vol. 73, No. 3, Nov. 2006, pp. 730-739.
International Search Report dated Aug. 14, 2013 issued in International Application No. PCT/EP2013/058335.
Lee et al., "A Mechanism-Based Inhibitor Targeting the $_{DD}$-Transpeptidase Activity of Bacterial Penicillin-Binding Proteins", Journal of the American Chemical Society, vol. 125, Dec. 2003, pp. 16322-16326.
Olukoya et al., "Plasmid profiles and antibiotic susceptibility patterns of Lactobacillus isolated from fermented foods in Nigeria," Food Microbiology, vol. 10, Aug. 1993, pp. 279-285.
Lu, Ye et al.; "Selection of Multi-resistance *Lactobacillus bulgaricus* Strain"; Journal of Dairy Science and Technology; 1:6-10 (Feb. 2010).
Fukuda et al.; "Exopolysaccharides from dairy lactic acid bacteria," Obihiro University Archives of Knowledge, 60: 66-92 (2010).
Mills et al.; "The changing face of dairy starter culture research: From genomics to economics," International Journal of Dairy Technology, 63(2):149-170 (May 2010).
Olukoya et al.; "Plasmid profiles and antibiotic susceptibility patterns of *Lactobacillus* isolated from fermented foods in Nigeria," Food Microbiology, 10(4):279-285 (Aug. 1993).
Patel et al.; "Isolation, characterization and mutagenesis of exopolysaccharide synthesizing new strains of lactic acid bacteria," The Internet Journal of Microbiology, 8(1):1-10 (2009).
D'Aimmo, et al., "Antibiotic resistance of lactic acid bacterial and *Bifidobacterium* spp. Isolated from dairy and pharmaceutical products, " *International Journal of Food Microbiology*, vol. 115, pp. 35-42 (Apr. 2007).
Klare et al., "Antimicrobial susceptibilities of *Lactobacillus, Pediococcus* and *Lactococcus* human isolates and cultures intended for probiotic or nutritional use," *Journal of Antimicrobial Chemotherapy*, vol. 59, pp. 900-912 (May 2007).

(Continued)

*Primary Examiner* — Amber R Orlando
*Assistant Examiner* — Philip A Dubois
(74) *Attorney, Agent, or Firm* — Foley & Lardner LLP

(57) ABSTRACT

The present invention relates to mutants of lactic acid bacteria which are resistant to the antibiotic ampicillin and which were found to give an increased texture when grown in milk while maintaining the other growth properties of the parent strain. The present invention, furthermore, relates to compositions comprising such mutants, and to dairy products fermented with the lactic acid bacteria resistant to ampicillin.

8 Claims, No Drawings

(56) References Cited

OTHER PUBLICATIONS

Mollet, "Genetically improved starter strains: opportunities for the dairy industry," International Dairy Journal, vol. 9, pp. 11-15 (1999).

Guzel-Seydim et al., "Influences of exopolysaccharide producing cultures on the quality of plain set type yogurt," Food Control, vol. 16, pp. 205-209 (2005).

* cited by examiner

AMPICILLIN RESISTANT TEXTURIZING LACTIC ACID BACTERIA STRAINS

CROSS REFERENCE TO RELATED APPLICATIONS

The present application is a divisional of U.S. patent application Ser. No. 14/395,615, filed Oct. 20, 2014, as the U.S. National Stage of International Application No. PCT/EP2013/058335, filed on Apr. 23, 2013, which claims the benefit of European Patent Application No. 12165134.3, filed on Apr. 23, 2012.

FIELD OF INVENTION

The present invention relates to mutants of lactic acid bacteria, such as *Lactobacillus delbrueckii* subsp. *bulgaricus* and *Streptococcus thermophilus*, which are resistant to the antibiotic ampicillin, and which were found to give an increased texture when grown in milk while maintaining the other growth properties of the parent strain. The present invention, furthermore, relates to cultures, such as starter cultures, comprising such mutants, and to dairy products fermented with the cultures.

BACKGROUND OF INVENTION

The food industry uses numerous bacteria, in particular lactic acid bacteria, in order to improve the taste and the texture of foods but also in order to extend the shelf life of these foods. In the case of the dairy industry, lactic acid bacteria are used intensively in order to bring about the acidification of milk (by fermentation) but also in order to texturize the product into which they are incorporated.

Among the lactic acid bacteria used in the food industry, there can be mentioned the genera *Streptococcus, Lactococcus, Lactobacillus, Leuconostoc, Pediococcus* and *Bifidobacterium*. The lactic acid bacteria of the species *Streptococcus thermophilus* are used extensively alone or in combination with other bacteria such as *Lactobacillus delbrueckii* subsp. *bulgaricus* for the production of food products, in particular fermented products. They are used in particular in the formulation of the ferments used for the production of fermented milks, for example yoghurts. Certain of them play a dominant role in the development of the texture of the fermented product. This characteristic is closely linked to the production of polysaccharides.

The current trend in yoghurts is for mild flavor and high texture. Today this is achieved by the use of cultures which produce a mild flavor and the addition of thickeners or protein to give the desired thickness. Yoghurt producers would like to be able to make yoghurt with these properties without the addition of thickening agents. This will help them reduce cost and give a cleaner label. One very attractive way to achieve this would be to have a starter culture which produces a high level of texture.

In order to meet the requirements of the industry, it has become necessary to provide novel texturizing strains of lactic acid bacteria, in particular of *Lactobacillus delbrueckii* subsp *bulgaricus* and *Streptococcus thermophilus*, for texturizing food products. Especially there is a need for novel texturizing strains of *Lactobacillus delbrueckii* subsp *bulgaricus* which can be used together with novel texturizing strains of *Streptococcus thermophilus*.

The inventors of the present invention has previously developed a novel selection method for the identification of improved lactic acid bacteria, such as *Lactobacillus delbrueckii* subsp. *bulgaricus* and *Streptococcus thermophilus* bacteria, which result in high texture when used for fermenting milk substrate for fermented milk products.

The method, which is described in International (PCT) patent application No. WO 2012/052557, relates to that the present inventors have identified a surprisingly relevant link between resistance to D-cycloserine and functionally equivalent antibiotics and improved texturizing properties of the lactic acid bacteria.

D-cycloserine (D-4-amino-isoxasolidone) is an antibiotic which inhibits alanine racemase, D-alanyl-D-alanine ligase, D-alanyl-alanine synthase and D-alanine permease causing cell lysis. D-alanine racemase is essential for the production of D-alanine, an integral part of the peptidoglycan layer of the cell wall.

Ampicillin is an antibiotic of the beta-lactam class of antibiotics and is effective against many gram-positive bacteria including most lactic acid bacteria. Ampicillin is a competitive inhibitor of enzymes of the DD-transpeptidase type (EC 3.4.16.4). Inhibition of DD-transpeptidase by ampicillin prevents the formation of a peptide bond required for the formation of the bacterial cell wall and ultimately leads to lysis of the cell.

Mutants resistant to ampicillin have been described for a number of different bacteria but—to the knowledge of the present inventors—there is in the prior art not described or suggested any herein relevant link between resistance to ampicillin and improved texturizing properties.

SUMMARY OF THE INVENTION

The inventors of the present invention have surprisingly found that a group of lactic acid bacteria mutants resistant to ampicillin generates high shear stress and/or gel stiffness when the bacteria are used for fermenting milk.

The present inventors have developed a method for obtaining such texturizing lactic acid bacteria strains which are resistant to the antibiotic ampicillin and/or another antibiotic which inhibits the enzyme DD-transpeptidase.

The herein described method for obtaining a lactic acid bacteria strain comprises the following two steps:
(I) first to screen and select for lactic acid bacteria strains which are resistant to ampicillin, one may term it a resistance to ampicillin that is significantly higher than normally present in natural/wildtype lactic acid bacteria; and
(ii) from the pool of ampicillin resistant strains identified in step (i) to screen and select for a lactic acid bacteria strains that has improved texturizing properties.

As shown in Example 2 herein, the present inventors found that from a pool of ampicillin resistant lactic acid bacteria strains it was relatively rapid to screen/select for a lactic acid bacteria strain that has improved texturizing properties. Essentially, the reason for this is that the present inventors have identified that a very high percentage of the ampicillin resistant lactic acid bacteria strain (selected in step (i)) also have improved texturizing properties.

Accordingly, the first screening and selection for resistance to ampicillin may be seen as a kind of pre-step to rapidly and efficiently be able to screen and select for a lactic acid bacteria strain that has improved texturizing properties.

As evident to the skilled person—a significant advantage of the herein described screening and selection method is that one relatively rapidly and efficiently is able to screen and select for a lactic acid bacteria strain that has improved texturizing properties. For instance, if one already has a lactic acid bacteria strain with commercially relevant properties in relation to e.g. low post-acidification when used in preparing fermented milk products, one can then use this strain as a starting cell for mutagenesis and then relatively rapidly select for and obtain a novel lactic acid bacteria strain that has improved texturizing properties while still maintaining its good properties with respect to e.g. low post-acidification.

As shown in Example 2 herein approximately 25% of the first selected ampicillin resistant strains also resulted in significantly higher texture as determined by an efflux time of 28 ml acidified milk from a polystyrene 25-ml pipette of at least 50 seconds.

It is submitted that without using the novel screening and selection method as described herein, it would not be possible (or it would take a very long time) to identify a lactic acid bacteria strain that results in such a long efflux time.

Without being limited to theory, a theoretical explanation for the herein surprisingly identified link between ampicillin resistance and improved texturizing properties could be that such ampicillin resistant lactic acid cells produce more of the so-called extracellular polysaccharides (EPS). It could then theoretically be that such EPS could give a kind of protection around the cell, i.e. that these EPS protect the cells against ampicillin entry into the cells and thereby give the increased ampicillin resistance.

Without being limited to theory, it could also be the increased production of EPS that result in the increased texture in milk fermented with the ampicillin resistant lactic acid bacteria.

As discussed above, the herein identified lactic acid bacteria strains are first selected for being resistant to ampicillin, i.e. resistant to ampicillin concentrations that are significantly higher than the ampicillin concentrations tolerated by natural/wildtype lactic acid bacteria.

In accordance with the above surprising findings, the present invention relates to texturizing lactic acid bacteria strains, such as *Lactobacillus delbrueckii* subsp *bulgaricus* and *Streptococcus thermophilus* strains, which are ampicillin resistant and/or resistant to another antibiotic which inhibits the enzyme DD-transpeptidase and a method for obtaining such strains. Furthermore, the present invention relates to cultures, such as starter cultures, comprising the mutants and to dairy products, such as fermented milk products fermented with the cultures.

DETAILED DISCLOSURE

Definitions

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

In the present context, a yoghurt starter culture is a bacterial culture which comprises at least one *Lactobacillus delbrueckii* subsp *bulgaricus* strain and at least one *Streptococcus thermophilus* strain. In accordance herewith, a "yoghurt" refers to a fermented milk product obtainable by inoculating and fermenting milk with a composition comprising a *Lactobacillus delbrueckii* subsp *bulgaricus* strain and a *Streptococcus thermophilus* strain.

By "texture" or "mouthfeel" are meant the product's physical and chemical interaction in the mouth.

Methods for determining the texture of milk include measuring the shear stress (viscosity), gel stiffness and ropiness of the fermented milk are readily available and known in the art and exemplified herein.

In the present context, the terms "shear stress", "gel stiffness" and "ropiness" determine viscosity.

Viscosity (unit is Pa s) is defined as Shear Stress (Pa)/Shear rate (1/s).

Shear stress value is reported as a standard herein at shear rate=300 1/s. Sensory experiments have shown (data not shown) that the best correlation between rheological measurements and sensory viscosity/mouth thickness are found when using the viscosity measured at shear rate 300 1/s.

The term "gel stiffness" or "gel firmness" is a measure of how long the structure of a fermented milk product is retained when it is subjected to pressure and is measured in 1 HZ (Pa)

The term "ropiness" as used herein refers to the formation of strings and threads and cohesiveness in the fermented milk product. Ropiness is defined and measured as described in Int. Dairy J. 16(2); 111-118 (Folkenberg et al. 2006).

The term "resistant to ampicillin" herein means that a particular mutated bacterial strain is not killed, or killed significantly more slowly compared to the corresponding non-mutated strain from which the mutated strain is derived in the presence of said antibiotic in the culture medium. Dependent on the concentration of the antibiotic compound in the culture medium, resistance can also be reflected by altered growth properties of the mutated and non-mutated strains. For example, a low concentration of the antibiotic in the culture medium will prevent or significantly decrease the growth of non-mutated strains while the growth of the mutated strains is not affected. Non-mutated strains which can be used as sensitive reference strains in the assessment of resistance preferably include the strain CHCC13995.

A lactic acid bacteria strain which is resistant to the antibiotic ampicillin, is herein defined as a lactic acid bacteria strain, wherein the amount of the antibiotic ampicillin that reduces the $OD_{500}$ measured growth, after 20 hours growth at 37° C., with 20% in a medium suitable for the growth of the lactic acid bacteria strain (e.g. MRS medium for *Lactobacillus delbrueckii* subsp. *bulgaricus* strains and M17 containing 2% (w/v) lactose for *Streptococcus thermophilus*) as compared to the OD600 measured growth in the medium without the antibiotic ampicillin is higher than 400 ng/ml.

A mutant lactic acid bacteria strain which is resistant to ampicillin is herein further defined by that the minimum inhibitory concentration (MIC) value read in an E-test is at least 1 increment higher for the mutant lactic acid bacteria strain than for the mother strain from where the mutant strain is derived.

In the present context, the term "mutant" should be understood as a strain derived, or a strain which can be derived from a strain of the invention (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or improved, properties (e.g. regarding viscosity, gel stiffness and ropiness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

In the present context, the term "variant" should be understood as a strain which is functionally equivalent to a strain of the invention, e.g. having substantially the same, or improved, properties e.g. regarding viscosity, gel stiffness and ropiness). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and aspects of the invention

As discussed herein a high percentage of lactic acid bacteria which are resistant to the antibiotic ampicillin were found to give an increased texture when grown in milk compared to a commercially relevant texturizing strain.

A person of skill in the art will recognize that other antibiotics with the same mode of action or the same targets as ampicillin can be used alone or in combination with ampicillin to isolate mutants of the type described herein. The present invention, therefore, also encompasses the use of such other functionally equivalent antibiotics, such as other inhibitors of DD-transpeptidase. Such antibiotics include, but are not limited to, amoxicillin, penicillin G, procaine penicillin, benzathine penicillin, and penicillin V.

In a first aspect, the present invention relates to a lactic acid bacteria strain characterized by that:

(i) the lactic acid bacteria strain is resistant to the antibiotic ampicillin and/or another antibiotic which inhibits the enzyme DD-transpeptidase, defined by that the amount of the antibiotic that reduces the $OD_{600}$ measured growth, after 20 hours growth at 37° C., with 20% in a medium suitable for growth of the lactic acid bacteria strain as compared to the $OD_{600}$ measured growth in the medium without the antibiotic is higher than 400 ng/ml; and (ii) the efflux time from a polystyrene 25-ml pipette of 28 ml of full fat cow milk containing 2% (w/v) skimmed milk powder, inoculated with at least $10^4$ CFU/ml of the lactic acid bacteria strain and acidified at 37° C. for 20 hours is at least 50 seconds. Preferably, the antibiotic of step (i) is ampicillin.

Both the assay for determining the amount of antibiotic which reduces the $OD_{600}$ measured growth by 20% of point (i) and the assay for determining the efflux time of 28 ml acidified milk from a polystyrene 25-ml pipette of point (ii) are based on known, commercially available standard elements.

The person of skill in the art will know of standard medium suitable for growth of the lactic acid bacteria strain, including MRS medium suitable for growth of *Lactobacillus delbrueckii* subsp. *bulgaricus* strains and M17 medium+2% (w/v) lactose suitable for growth of *Streptococcus thermophilus* strains as exemplified herein.

Accordingly, based on the detailed description of the assays herein (see e.g. Example 2) the skilled person is routinely able to repeat these assays to objectively determine whether a specific lactic acid bacteria strain of interest complies with being resistant to ampicillin and/or another antibiotic which inhibits DD-transpeptidase (of point (i)) and with having improved texturizing properties (of point (ii)).

In a preferred embodiment the lactic acid bacteria strain is selected from the group consisting of *Lactobacillus delbrueckii* subsp. *bulgaricus* and *Streptococcus thermophilus*. In a more preferred embodiment the lactic acid bacteria strain is a *Lactobacillus delbrueckii* subsp. *bulgaricus* strain.

In preferred embodiments the amount of the antibiotic that reduces the $OD_{600}$ measured growth with 20% of point (i) is higher than 500 ng/ml, such as higher than 600 ng/ml, such as higher than 700 ng/ml.

In other preferred embodiments the efflux time of point (ii) is at least 60 seconds, such as at least 70 seconds, such as at least 80 seconds, such as at least 90 seconds, such as at least 100 seconds, such as at least 110 seconds.

In a second aspect, the present invention relates to a lactic acid bacteria strain characterized by that:

(i) the lactic acid bacteria strain is resistant to the antibiotic ampicillin and/or another antibiotic which inhibits the enzyme DD-transpeptidase, defined by that the Minimum Inhibitory Concentration (MIC) for the mutant lactic acid bacteria strain is at least 1 increment higher in an E-test than the MIC for the mother strain from which the lactic acid bacteria strain is derived; and (ii) the efflux time from a polystyrene 25-ml pipette of 28 ml of full fat cow milk containing 2% (w/v) skimmed milk powder, inoculated with at least $10^4$ CFU/ml of the mutant lactic acid bacteria strain and acidified at 37° C. for 20 hours, is at least double the time as the efflux time from a polystyrene 25-ml pipette of 28 ml of full fat cow milk containing 2% (w/v) skimmed milk powder, inoculated with at least $10^4$ CFU/ml of the mother strain and acidified at 37° C. for 20 hours.

Preferably, the antibiotic of step (i) is ampicillin.

Both the E-test of point (i) and the assay for determining the efflux time of 28 ml acidified milk from a polystyrene 25-ml pipette of point (ii) are based on known, commercially available standard elements.

Accordingly, based on the detailed description of the assays herein (see e.g. Example 1 and Example 2) the skilled person is routinely able to repeat these assays to objectively determine whether a specific lactic acid bacteria strain of interest complies with being resistant to ampicillin and/or another antibiotic which inhibits DD-transpeptidase (of point (i)) and with having improved texturizing properties (of point (ii)).

In a preferred embodiment the lactic acid bacteria strain is selected from the group consisting of *Lactobacillus delbrueckii* subsp. *bulgaricus* and *Streptococcus thermophilus*. In a more preferred embodiment the lactic acid bacteria strain is a *Lactobacillus delbrueckii* subsp. *bulgaricus* strain.

In preferred embodiments the MIC for the mutant lactic acid bacteria strain of point (i) is at least 2 increments, such as at least 3 increments, such as at least 4 increments, such as at least 5 increments, higher in an E-test than the MIC for the mother strain.

In other preferred embodiments the efflux time of point (ii) is at least 50 seconds, such as at least 60 seconds, such as at least 70 seconds, such as at least 80 seconds, such as at least 90 seconds, such as at least 100 seconds, such as at least 110 seconds.

A third aspect of the present invention is directed to a lactic acid bacteria strain selected from the group consisting of the *Lactobacillus delbrueckii* subsp. *bulgaricus* strain CHCC15466 that was deposited with the Deutsche Sammlung von Mikroorganismen and Zellkulturen under accession number DSM 25852 and mutants and variants derived thereof.

It is clear for the skilled person that by using the deposited strain as starting material, the skilled person can routinely, by conventional mutagenesis or re-isolation techniques, obtain further mutants or derivatives thereof that retain the herein described relevant features and advantages. Accordingly, the term "mutants derived thereof" relates to mutant strains obtained by using the deposited strain as starting material and wherein the mutants retain the essential property of the deposited strain, wherein said essential property is that the efflux time of 28 ml of full fat cow milk containing 2% (w/v) skimmed milk powder, inoculated with at least $10^4$ CFU/ml of the lactic acid bacteria strain and acidified at 37° C. for 20 hours, from a polystyrene 25-ml pipette is at least 50 seconds.

A fourth aspect of the present invention relates to a composition comprising from $10^4$ to $10^{14}$ CFU/g of a lactic acid bacteria strain according to any of claims 1 to 6.

In a preferred embodiment the composition comprises at least one *Lactobacillus delbrueckii* subsp. *bulgaricus* strain. Preferably, the composition comprises at least one *Lactobacillus delbrueckii* subsp. *bulgaricus* strain and at least one *Streptococcus thermophilus* strain.

In another preferred embodiment the composition is usable as a starter culture.

In yet another preferred embodiment the composition is in frozen, freeze-dried or liquid form.

The lactic acid bacteria strain (which is resistant to ampicillin and/or another antibiotic which inhibits DD-transpeptidase and which has improved texturizing properties) according to the present invention may preferably be used for preparing a fermented milk product. The dose and administration may be done according to the art.

Further, all other herein relevant steps for making a fermented milk product may be done according to the art. Such other relevant steps for preparing fermented milk products are well known routine steps for the skilled person.

Accordingly, a fifth aspect of the present invention relates to a method for preparing a fermented milk product, comprising fermenting a milk substrate with the lactic acid bacteria strain according to the first, second or third aspect of the invention or the composition according to the fourth aspect of the present invention.

A sixth aspect relates to a fermented milk product obtainable by the method according to the fourth aspect of the invention.

A seventh aspect relates to a fermented milk product comprising the lactic acid bacteria strain according to the first, second or third aspect of the invention or the composition according to the fourth aspect of the invention.

An eighth aspect of the present invention is directed to use of the lactic acid bacteria strain according to the first, second or third aspect of the invention or the composition according to the fourth aspect of the invention for the preparation of a dairy product.

In a preferred embodiment the dairy product is a fermented milk product. Preferably, the fermented milk product is a yoghurt.

A ninth aspect of the present invention relates to a method for obtaining a lactic acid bacteria strain, said method comprising:
  a) selecting and isolating from a pool of lactic acid bacteria strains a pool of lactic acid bacteria strains which are resistant to the antibiotic ampicillin and/or to another antibiotic which inhibits the enzyme DD-transpeptidase, defined by that the amount of the antibiotic that reduces the $OD_{600}$ measured growth, after 20 hours growth at 37° C., with 20% in a medium suitable for growth of the lactic acid bacteria strain as compared to the growth in the medium without the antibiotic is higher than 400 ng/ml; and
  b) selecting and isolating, from the pool of lactic acid bacteria strains which are resistant to ampicillin and/or to another antibiotic which inhibits the enzyme DD-transpeptidase of step a), a lactic acid bacteria strain wherein the efflux time of 28 ml of full fat cow milk containing 2% (w/v) skimmed milk powder, inoculated with at least $10^4$ CFU/ml of the lactic acid bacteria strain and acidified at 37° C. for 20 hours from a polystyrene 25-ml pipette is at least 50 seconds.

Preferably, the method comprises:
  a) selecting and isolating from a pool of lactic acid bacteria strains a pool of lactic acid bacteria strains which are resistant to the antibiotic ampicillin, defined by that the amount of ampicillin that reduces the $OD_{600}$ measured growth, after 20 hours growth at 37° C., with 20% in a medium suitable for growth of the lactic acid bacteria strain as compared to the growth in the medium without ampicillin is higher than 400 ng/ml; and
  b) selecting and isolating, from the pool of lactic acid bacteria strains which are resistant to the antibiotic ampicillin of step a), a lactic acid bacteria strain wherein the efflux time of 28 ml of full fat cow milk containing 2% (w/v) skimmed milk powder, inoculated with at least $10^4$ CFU/ml of the lactic acid bacteria strain and acidified at 37° C. for 20 hours from a polystyrene 25-ml pipette is at least 50 seconds.

In a preferred embodiment the lactic acid bacteria strain is selected from the group consisting of *Lactobacillus delbrueckii* subsp. *bulgaricus* and *Streptococcus thermophilus*. In a more preferred embodiment the lactic acid bacteria strain is a *Lactobacillus delbrueckii* subsp. *bulgaricus* strain.

In preferred embodiments the amount of the antibiotic that reduces the $OD_{600}$ measured growth with 20% of point (i) is higher than 500 ng/ml, such as higher than 600 ng/ml, such as higher than 700 ng/ml.

In other preferred embodiments the efflux time of point (ii) is at least 60 seconds, such as at least 70 seconds, such as at least 80 seconds, such as at least 90 seconds, such as at least 100 seconds, such as at least 110 seconds.

A tenth aspect is directed to a method for obtaining a lactic acid bacteria strain, said method comprising:
  a) providing a lactic acid bacteria mother strain;
  b) selecting and isolating a pool of mutant lactic acid bacteria strains which are resistant to the antibiotic ampicillin and/or to another antibiotic which inhibits the enzyme DD-transpeptidase, defined by that the Minimum Inhibitory Concentration (MIC) for the mutant lactic acid bacteria strains is at least 1 increment higher in an E-test than the MIC for the mother strain from which the mutant lactic acid bacteria strains are derived; and
  c) selecting and isolating, from the pool of mutant lactic acid bacteria strains which are resistant to ampicillin and/or to another antibiotic which inhibits the enzyme DD-transpeptidase of step b), a mutant lactic acid bacteria strain wherein the efflux time from a polystyrene 25-ml pipette of 28 ml of full fat cow milk containing 2% (w/v) skimmed milk powder, inoculated with at least $10^4$ CFU/ml of the mutant lactic acid bacteria strain and acidified at 37° C. for 20 hours is at least double the time as the efflux time from a polystyrene 25-ml pipette of 28 ml of full fat cow milk containing 2% (w/v) skimmed milk powder, inoculated with at least $10^4$ CFU/ml of the mother strain and acidified at 37° C. for 20 hours.

Preferably, the method comprises:
  a) providing a lactic acid bacteria mother strain;
  b) selecting and isolating a pool of mutant lactic acid bacteria strains which are resistant to the antibiotic ampicillin, defined by that the Minimum Inhibitory Concentration (MIC) for the mutant lactic acid bacteria strains is at least 1 increment higher in an E-test than the MIC for the mother strain from which the mutant lactic acid bacteria strains are derived; and
  c) selecting and isolating, from the pool of mutant lactic acid bacteria strains which are resistant to ampicillin of step b), a mutant lactic acid bacteria strain wherein the efflux time from a polystyrene 25-ml pipette of 28 ml of full fat cow milk containing 2% (w/v) skimmed milk powder, inoculated with at least $10^4$ CFU/ml of the mutant lactic acid bacteria strain and acidified at 37° C. for 20 hours is at least double the time as the efflux time from a polystyrene 25-ml pipette of 28 ml of full fat cow milk containing 2% (w/v) skimmed milk powder, inoculated with at least $10^4$ CFU/ml of the mother strain and acidified at 37° C. for 20 hours.

In a preferred embodiment the lactic acid bacteria mother strain is selected from the group consisting of *Lactobacillus delbrueckii* subsp. *bulgaricus* and *Streptococcus thermophilus*. In a more preferred embodiment the lactic acid bacteria strain is a *Lactobacillus delbrueckii* subsp. *bulgaricus* strain.

In an even more preferred embodiment of the present invention the mother strain is the *Lactobacillus delbrueckii* subsp. *bulgaricus* strain CHCC13995 that was deposited with Deutsche Sammlung von Mikroorganismen and Zellkulturen with the accession number DSM 24021.

In preferred embodiments the MIC for the mutant lactic acid bacteria strain of point (i) is at least 2 increments, such as at least 3 increments, such as at least 4 increments, such as at least 5 increments, higher in an E-test than the MIC for the mother strain.

In other preferred embodiments the efflux time of point (ii) from a polystyrene 25-ml pipette of 28 ml full fat cow milk containing 2% (w/v) skimmed milk powder, inoculated with at least $10^4$ CFU/ml of the mutant lactic acid bacteria strain and acidified at 37° C. for 20 hours is at least 50 seconds, such as at least 60 seconds, such as at least 70 seconds, such as at least 80 seconds, such as at least 90 seconds, such as at least 100 seconds, such as at least 110 seconds.

In an eleventh aspect the present invention relates to a lactic acid bacteria strain obtainable by a method according to the eighth or ninth aspect of the invention.

The present invention is further illustrated by the following non-limiting examples.

EXAMPLES

Materials:
Media: For *Streptococcus thermophilus*, suitable media include the known M17 agar medium having the following composition:
agar, 12.75 g/L
ascorbic acid, 0.5 g/L
casein peptone (tryptic), 2.5 g/L
disodium β-glycerophosphate pentahydrate, 19 g/L
magnesium sulfate hydrate, 0.25 g/L
meat extract, 5 g/L
meat peptone (peptic), 2.5 g/L
soyapeptone (papainic), 5 g/L
yeast extract, 2.5 g/L
and M17 broth medium with this composition:
ascorbic acid, 0.5 g/L
lactose, 5 g/L
magnesium sulfate, 0.25 g/L
meat extract, 5 g/L
meat peptone (peptic), 2.5 g/L
sodium glycerophosphate, 19 g/L
soya peptone (papainic), 5 g/L
tryptone, 2.5 g/L
yeast extract, 2.5 g/L
final pH 7.0±0.2 (25° C.)

These media are normally used following the addition of 20 g/l of lactose (2% w/v). For *Lactobacillus delbrueckii* subsp. *bulgaricus*, suitable media include the known MRS medium.

MRS agar medium has the following composition:

| | |
|---|---|
| Bacto Proteose Peptone no. 3 | 10 g/l |
| Bacto Beef Extract | 10 g/l |
| Bacto Yeast Extract | 5 g/l |
| Dextrose | 20 g/l |
| Sorbitan Monooleate Complex | 1 g/l |
| Ammonium Citrate | 2 g/l |
| Sodium acetate | 5 g/l |
| Magnesium sulphate | 0.1 g/l |
| Manganese sulphate | 0.05 g/l |
| Potassium Phosphate Dibasis | 2 g/l |
| Bacto Agar | 15 g/l | and MRS broth medium has this composition:

| | |
|---|---|
| Bacto Proteose Peptone no. 3 | 10 g/l |
| Bacto Beef Extract | 10 g/l |
| Bacto Yeast Extract | 5 g/l |
| Dextrose | 20 g/l |
| Sorbitan Monooleate Complex | 1 g/l |
| Ammonium Citrate | 2 g/l |
| Sodium acetate | 5 g/l |
| Magnesium sulphate | 0.1 g/l |
| Manganese sulphate | 0.05 g/l |
| Potassium Phosphate Dibasis | 2 g/l |
| final pH 6.5 ± 0.2 (25° C.) | |

As known to the skilled person, the M17 medium is a medium that is considered to be suitable for growth of *Streptococcus thermophilus* and the MRS medium is a medium that is considered to be suitable for growth of *Lactobacillus delbrueckii* subsp. *bulgaricus*.

In the present context and as understood by the skilled person, the specific M17 and MRS media concentrate may be supplied from different suppliers and independently of the specific supplier one will (within standard measurement uncertainty) get the same herein relevant result of ampicillin resistance for a herein relevant strain of interest.

Example 1

Ampicillin Resistance Selection Assay

The method is illustrated using a strain of *Lactobacillus delbrueckii* subsp. *bulgaricus*. To carry out the ampicillin resistance selection assay with *Streptococcus thermophilus*, M17 medium with lactose added to 2% w/v should be used instead of MRS medium.

A *Lactobacillus delbrueckii* subsp. *bulgaricus* strain of interest is inoculated into 10 ml MRS broth medium and grown for at least 20 hours at 37° C. under anaerobic conditions. A cotton swab is dipped in the culture and used to streak out on the entire surface of a MRS agar plate (90 mm in diameter). An ampicillin E-test stick (0.016-256 μg/ml) for Antimicrobial Susceptibility Testing (Biomerieux, cat. #501558) is placed on top of the agar, and the plate is incubated for not more than 24 hours at 37° C. under anaerobic conditions. The minimum inhibitory concentration (MIC) of ampicillin is the lowest concentration that will inhibit the visible growth of the plated strain and is read at the point where the elliptical zone of inhibition intersects the E-test strip.

A *Lactobacillus delbrueckii* subsp. *bulgaricus* cell that has an increased resistance to ampicillin as discussed herein, is herein defined as a *Lactobacillus delbrueckii* subsp. *bulgaricus* cell, where the MIC value read is at least 1 increment higher as noted on the E-strip than for the mother strain.

Cells that are capable of complying with this increased resistance to ampicillin criteria are herein defined as cells that are resistant to ampicillin in the ampicillin resistance assay of this Example 1.

Conclusion:
Based on the ampicillin resistance Selection assay of this Example 1—for a specific strain of interest (e.g. one from a relevant commercial product)—the skilled person can routinely test if this specific strain of interest has the herein relevant ampicillin resistance.

Example 2

Use of Ampicillin to Isolate Mutants of *Lactobacillus delbrueckii* subsp. *bulgaricus* with Improved Rheological Properties Strains:
*Lactobacillus delbrueckii* subsp. *bulgaricus* CHCC13995
*Lactobacillus delbrueckii* subsp. *bulgaricus* CHCC15466 (ampicillin resistant mutant of CHCC13995)
Mutant Isolation:
In order to isolate ampicillin resistant mutants of the *Lactobacillus delbrueckii* subsp. *bulgaricus* strain CHCC13995, cells derived from the growth of a single colony were inoculated anaerobically into 10 ml MRS broth containing one of the following amounts of ampicillin, 0 ng/ml, 100 ng/ml, 200 ng/ml, 300 ng/ml, 400 ng/ml, 500 ng/ml, 600 ng/ml or 700 ng/ml, and grown for at least 20 hours at 37° C.

After the 20 hours of growth $OD_{600}$ is measured for all samples.

Typically the concentration of ampicillin that reduces the $OD_{600}$ measured anaerobic growth of *Lactobacillus delbrueckii* subsp. *bulgaricus* with at least 20% as compared to the growth in MRS medium without ampicillin (i.e. with 0 ng/ml ampicillin) is higher than 300 ng/ml. Cultures where the concentration of ampicillin was 500 ng/ml were diluted and plated on MRS agar plates with no ampicillin added and then incubated anaerobically for at least 20 hours at 37° C. Colonies were then picked and screened for anaerobic growth at 37° C. in microtiter plates in the presence of 500 ng/ml ampicillin. Typically, 25% of the resulting colonies were identified as fast growers in the presence of ampicillin. These were chosen for further study. The selected ampicillin resistant mutants were further purified and tested for their ability to grow in milk. During this work it was observed that some of the mutants produced considerably more texture than the parent strain under these conditions.

Viscocity Screening:

A rheological screening analysis was done by using a simple pipette viscosity test. In this test the ampicillin resistant mutants were pre-tested for their viscosity (before real rheology testing) by measuring the efflux time from a polystyrene 25-ml pipette (CELLSTAR®) loaded with 28 ml of acidified milk:

For each sample, full fat cow milk which was added 2% (w/v) skimmed milk powder where inoculated with an ampicillin resistant mutant in an amount of at least $10^4$ cells per ml of milk and left to acidify for 20 hours at 37° C.

Before the pipetting test, the acidified milk was gently homogenized by stirring before loading into a polystyrene 25-ml pipette to the top (28 ml) and for each sample the efflux time from the pipette was measured 3 times. Table 1 lists the result of the pipette viscosity test on milk fermented at 37° C. for 20 hours by 21 ampicillin resistant mutants. The results show that most of these mutants result in a higher viscosity than mother strain. 6 out of the 21 ampicillin resistant mutants result in an efflux time which is double that of the mother strain and approximately 25% of the ampicillin resistant mutants result in an efflux time of at least 50 seconds.

Especially mutant 18 (amp mut 18) have a high efflux time. This mutant derivative was designated CHCC15466 and was used for rheological test described in Example 3.

Conclusion

The *Lactobacillus delbrueckii* subsp. *bulgaricus* ampicillin resistant mutants described herein may be incorporated into a culture, such as a starter culture, which produces a desirable high level of texture.

Example 3

Use of *Streptococcus thermophilus* and *Lactobacillus delbrueckii* subsp *bulgaricus* ampicillin resistant mutants for preparation of a fermented milk product.

Rheology:

Rheology analyses were carried on a StressTech rheometer from ReoLogica Instruments AB, Sweden, following growth in full fat cow milk with 2% (w/v) added skimmed milk powder.

The examples described above illustrate the improved texture of fermented milks fermented with selected ampicillin resistant mutants as single culture. In this example we will analyze the texture of fermented milks made as yoghurts i.e. with strains of *Streptococcus thermophilus* and *Lactobacillus delbrueckii* subsp *bulgaricus* used in combination. To document the improved texturizing effect of some of the mutants, yoghurts were made with combinations of one fixed wild type *Streptococcus thermophilus* strain CHCC4895 mixed with a *Lactobacillus delbrueckii* subsp *bulgaricus* wild type strain CHCC13995 and an ampicillin resistant strain CHCC15466, respectively. The yoghurt cultures were mixed at a ratio of 9:1 of *Streptococcus thermophilus: Lactobacillus delbrueckii* subsp *bulgaricus* and inoculated into full fat cow milk with 2% added skimmed milk powder and fermented at 40° C. to a final pH of 4.50. The following mixtures were analyzed after 5 days storage at 4° C. using the Stresstech rheometer. Ropiness is measured as described by Folkenberg et al. (2006. Int. Dairy J. 16(2); 111-118) The results are presented in Table 2.

TABLE 2

Rheological measurements of yoghurts made with *Streptococcus thermophilus* strain CHCC4896 and either *Lactobacillus delbrueckii* subsp. *bulgaricus* strain CHCC13995 or ampicillin resistant *Lactobacillus delbrueckii* subsp. *bulgaricus* strain CHCC15466.

| Sample | Shear stress at 300 1/s (Pa) | Gel stiffness at 1 HZ (Pa) | Ropiness (Pa/Pa) |
|---|---|---|---|
| CHCC4895 + CHCC13995 | 35.8 | 171 | 0.382 |
| CHCC4895 + CHCC15466 | 35 | 193 | 0.422 |

TABLE 1

Efflux time (average of 3 measurements) measured in seconds from a polystyrene 25-ml pipette loaded with 28 ml of acidified milk

| Strain | CHCC13995 | mut 1 | mut 2 | mut 3 | mut 4 | mut 5 | mut 6 | mut 7 | mut 8 | mut 9 |
|---|---|---|---|---|---|---|---|---|---|---|
| Efflux time (s) | 22 | 41 | 38 | 79.5 | 49 | 22 | 40.5 | 33.5 | 40 | 26.5 |

| Strain | mut 10 | mut 11 | mut 12 | mut 13 | mut 14 | mut 15 | mut 16 | mut 17 | mut 18 | mut 19 |
|---|---|---|---|---|---|---|---|---|---|---|
| Efflux time (s) | 42 | 39 | 49 | 43 | 77 | 39 | 94 | 56 | 116 | 49 |

| Strain | mut 20 | mut 21 |
|---|---|---|
| Efflux time (s) | 33 | 33.5 |

The results clearly show that the improved texturizing property of the ampicillin resistant mutant CHCC15466 as observed with the single cultures was preserved also in the presence of a strain of *Streptococcus thermophilus*.

While the shear stress is only slightly affected, the gel stiffness and the ropiness are improved significantly where the mutant is used instead of the wild type strain of *Lactobacillus delbrueckii* subsp *bulgaricus* for the yoghurt fermentation.

Conclusion

The *Lactobacillus delbrueckii* subsp. *bulgaricus* ampicillin resistant mutant described herein may be incorporated into a culture, such as a starter culture, which produces a desirable high level of texture in a fermented milk product such as yoghurt.

Deposits and Expert Solution

The strain of *Streptococcus thermophilus* CHCC4895 was deposited with Deutsche Sammlung von Mikrooganismen und Zellkulturen GmbH (DSMZ), Inhoffenstr. 7B, D-38124 Braunschweig, Germany on 29 Mar. 2007 under the accession number DSM 19242.

The strain of *Lactobacillus delbrueckii* subsp. *bulgaricus* CHCC13995 was deposited with Deutsche Sammlung von Mikroorganismen und Zellkulturen GmbH, Inhoffenstr. 7B, D-38124 Braunschweig, Germany on 22 Sep. 2010 under the accession number DSM 24021.

The strain of *Lactobacillus delbrueckii* subsp. *bulgaricus* CHCC15466 was deposited with Deutsche Sammlung von Mikroorganismen und Zellkulturen GmbH, Inhoffenstr. 7B, D-38124 Braunschweig, Germany on 3 Apr. 2012 under the accession number DSM 25852

The deposits have been made under the conditions of the Budapest Treaty on the International Recognition of the Deposit of Microorganisms for the Purposes of Patent Procedure.

The Applicant requests that a sample of the deposited microorganisms should be made available only to an expert approved by the Applicant.

The invention claimed is:

1. A method for obtaining a mutant texturizing lactic acid bacteria strain, comprising:
    (a) selecting and isolating, from a pool of lactic acid bacteria strains obtained from a mother strain without genetic engineering, a pool of mutant lactic acid bacteria strains which are resistant to the antibiotic ampicillin as determined by the amount of ampicillin that reduces the $OD_{600}$ measured growth of the lactic acid bacteria strain, after 20 hours growth at 37° C. in a medium suitable for growth of the lactic acid bacteria strain, by 20% as compared to the $OD_{600}$ measured growth in the medium without ampicillin being higher than 400 ng/ml; and
    (b) selecting and isolating from the pool of mutant lactic acid bacteria strains which are resistant to ampicillin a mutant lactic acid bacteria strain that exhibits a texturing property such that the efflux time of 28 ml of full fat cow milk containing 2% (w/v) skimmed milk powder, inoculated with at least $10^4$ CFU/ml of the lactic acid bacteria strain and acidified at 37° C. for 20 hours, from a polystyrene 25-ml pipette is at least 50 seconds.

2. A method according to claim 1, wherein the lactic acid bacteria strain is a strain of *Lactobacillus delbrueckii* subsp. *bulgaricus*.

3. A method according to claim 1, wherein the lactic acid bacteria strain is a strain of *Streptococcus* thermophiles.

4. A method according to claim 1, wherein the mother strain is *Lactobacillus delbrueckii* subsp. *bulgaricus* strain CHCC13995 that was deposited with the Deutsche Sammlung von Mikroorganismen and Zellkulturen, Braunschweig, Germany (DSMZ) under accession number DSM 24021.

5. A method according to claim 1, wherein the pool of mutant lactic acid bacteria strains obtained from the mother strain exhibit a Minimum Inhibitory Concentration (MIC) that is at least 1 increment higher in an E-test than that of the mother strain.

6. A method according to claim 1, wherein the mutant lactic acid bacteria strain exhibits a texturing property such that the efflux time of 28 ml of full fat cow milk containing 2% (w/v) skimmed milk powder, inoculated with at least $10^4$ CFU/ml of the lactic acid bacteria strain and acidified at 37° C. for 20 hours, from a polystyrene 25-ml pipette is at double the efflux time of the mother strain.

7. A method according to claim 1, wherein the mother strain is *Lactobacillus delbrueckii* subsp. *bulgaricus* strain CHCC15466 deposited with the DSMZ under accession number DSM 25852.

8. A method according to claim 7, wherein the mutant strain is a mutant or variant of *Lactobacillus delbrueckii* subsp. *bulgaricus* strain CHCC15466 deposited with the DSMZ under accession number DSM 25852.

* * * * *